(12) United States Patent
Carrigan

(10) Patent No.: US 12,226,241 B2
(45) Date of Patent: Feb. 18, 2025

(54) ASSEMBLY AND METHOD FOR SUPPORTING INSTRUMENTS DURING SPINAL SURGERY

(71) Applicant: Brandon Carrigan, McLoud, OK (US)

(72) Inventor: Brandon Carrigan, McLoud, OK (US)

( * ) Notice: Subject to any disclaimer, the term of this patent is extended or adjusted under 35 U.S.C. 154(b) by 0 days.

(21) Appl. No.: 18/454,479

(22) Filed: Aug. 23, 2023

(65) Prior Publication Data

US 2024/0065795 A1    Feb. 29, 2024

Related U.S. Application Data

(60) Provisional application No. 63/373,512, filed on Aug. 25, 2022.

(51) Int. Cl.
| | |
|---|---|
| A61B 50/22 | (2016.01) |
| A61B 5/33 | (2021.01) |
| A61B 50/33 | (2016.01) |

(52) U.S. Cl.
CPC .............. *A61B 50/22* (2016.02); *A61B 50/33* (2016.02)

(58) Field of Classification Search
CPC .. A61B 50/22; A61B 50/33; A61B 2050/3008
See application file for complete search history.

(56) References Cited

U.S. PATENT DOCUMENTS

| | | | |
|---|---|---|---|
| 2,903,129 A | 9/1959 | Anderson, III | |
| 3,116,828 A * | 1/1964 | Glassman | A61B 50/20 D24/229 |
| 3,467,247 A | 9/1969 | Weiss | |
| 3,634,937 A | 1/1972 | Green | |
| 3,696,920 A * | 10/1972 | Lahay | A61B 50/30 206/370 |
| 3,819,039 A | 6/1974 | Erickson | |
| 3,868,016 A * | 2/1975 | Szpur | A61B 50/33 211/DIG. 1 |
| 4,229,420 A | 10/1980 | Smith et al. | |
| 4,485,919 A | 12/1984 | Sandel | |
| 4,577,755 A | 3/1986 | Ramsay | |
| 4,643,303 A | 2/1987 | Arp et al. | |
| D306,481 S | 3/1990 | Lang | |
| 4,971,271 A * | 11/1990 | Sularz | F16L 3/223 248/68.1 |
| 5,046,624 A | 9/1991 | Murphy et al. | |
| D321,249 S | 10/1991 | Gorski | |
| 5,201,430 A | 4/1993 | Artzer | |
| 5,226,892 A * | 7/1993 | Boswell | A61M 25/02 24/616 |
| 5,368,161 A | 11/1994 | Plais | |

(Continued)

*Primary Examiner* — Stanton L Krycinski
(74) *Attorney, Agent, or Firm* — Dunlap Codding, P.C.

(57) ABSTRACT

An assembly including a receptacle having a cavity and a support member positioned within the cavity. The support member has a plurality of grooves and ridges that extend from a front end to a rear end. The grooves extend below a top end of a front wall of the receptacle. A surgical instrument is positioned on a top surface of the support member. The proximal end of the surgical instrument is positioned in one of the grooves of the support member and a distal end of the surgical instrument is positioned on a top end of a front wall of the receptacle such that a rear handle member and a forward handle member of the instrument extend vertically away from the support member.

17 Claims, 4 Drawing Sheets

(56) References Cited

U.S. PATENT DOCUMENTS

| | | | | |
|---|---|---|---|---|
| 5,381,896 | A * | 1/1995 | Simons | A61B 50/20 |
| | | | | 206/370 |
| 5,422,067 | A * | 6/1995 | Barney | A61B 50/33 |
| | | | | 422/20 |
| 5,451,380 | A | 9/1995 | Zinnanti | |
| D378,408 | S | 3/1997 | Pyeatt et al. | |
| 5,725,097 | A * | 3/1998 | Bettenhausen | A61L 2/26 |
| | | | | 292/210 |
| 5,762,202 | A * | 6/1998 | Atad | A61B 50/33 |
| | | | | 206/370 |
| 6,244,447 | B1 | 6/2001 | Frieze et al. | |
| 6,367,637 | B1 * | 4/2002 | Davis | A61B 50/20 |
| | | | | 211/184 |
| 6,426,041 | B1 | 7/2002 | Smith | |
| 6,436,357 | B1 * | 8/2002 | Frieze | A61L 2/26 |
| | | | | 422/292 |
| 6,629,615 | B2 * | 10/2003 | Kim | F16L 3/223 |
| | | | | 211/85.13 |
| 6,969,498 | B1 * | 11/2005 | Riley | A61B 50/20 |
| | | | | 206/370 |
| 7,066,328 | B2 | 6/2006 | Pulsifer | |
| 7,303,568 | B2 * | 12/2007 | Jannot | A61B 17/06061 |
| | | | | 606/148 |
| 8,162,156 | B1 | 4/2012 | Crisman | |
| 8,505,748 | B2 | 8/2013 | Jones et al. | |
| 8,523,824 | B2 * | 9/2013 | Teirstein | A61M 25/02 |
| | | | | 604/174 |
| 8,997,985 | B2 | 4/2015 | Reeves et al. | |
| 9,782,231 | B2 | 10/2017 | Freerks | |
| 10,420,624 | B2 | 9/2019 | Cerda et al. | |
| 10,456,210 | B2 * | 10/2019 | Jung | A61B 46/23 |
| 11,191,603 | B1 | 12/2021 | Schor | |
| 11,931,476 | B2 * | 3/2024 | Görz | A61B 50/30 |
| 2004/0206711 | A1 | 10/2004 | Hoftman | |
| 2004/0222175 | A1 | 11/2004 | Keating et al. | |
| 2005/0040066 | A1 | 2/2005 | Pulsifer | |
| 2005/0061696 | A1 | 3/2005 | Swank | |
| 2006/0076254 | A1 | 4/2006 | Corbitt, Jr. et al. | |
| 2008/0011699 | A1 | 1/2008 | Lyons | |
| 2010/0217246 | A1 | 8/2010 | Reeves et al. | |
| 2015/0010440 | A1 | 1/2015 | Roudebush et al. | |
| 2016/0066997 | A1 | 3/2016 | Ren et al. | |
| 2018/0318032 | A1 * | 11/2018 | DiSilvestro | A61B 50/20 |
| 2019/0008602 | A1 | 1/2019 | Cerda et al. | |

* cited by examiner

ASSEMBLY AND METHOD FOR SUPPORTING INSTRUMENTS DURING SPINAL SURGERY

CROSS-REFERENCE TO RELATED APPLICATIONS

The present application claims the benefit of U.S. Provisional Application Ser. No. 63/373,512, filed Aug. 25, 2022, which is hereby expressly incorporated by reference herein in its entirety.

BACKGROUND

Surgical instruments used during a surgical procedure are typically placed on a top surface of a Mayo stand. Often, at least one towel is placed on the top surface of the Mayo stand, and the surgical instruments are positioned in various places on the surface of the towel. Surgical instruments used during spinal surgery, such as Kerrison and pituitary rongeurs, are typically positioned laterally on the surface of the Mayo stand for use by the surgeon. This technique of placing the surgical instruments used in spinal surgery has several drawbacks. The loose positioning of the surgical instruments on the towel may cause the instruments to be inadvertently moved, slowing the timely selection of the surgical instrument for use during surgery. In other cases, the loose positioning of the surgical instruments on the towel may also be knocked off the Mayo stand onto the floor, eliminating the sterile surgical field.

In other cases, the surgical instruments used during spinal surgery may be positioned in an organizer on the Mayo stand's surface. However, the configuration and materials used in constructing the organizers on the market do not allow for the instruments used in spinal surgery to be timely selected for use during surgery. Therefore, there is a need for an assembly and method for supporting instruments that may be used during spinal surgery, that will hold the instruments used during spinal surgery securely, and that will permit the instruments to be identified and accessed promptly.

DETAILED DESCRIPTION OF EXEMPLARY EMBODIMENTS

The following detailed description refers to the accompanying drawings. The same reference numbers in different drawings may identify the same or similar elements.

The present disclosure describes an assembly and method for supporting at least one surgical instrument during spinal surgery.

As used herein, the terms "comprises," "comprising," "includes," "including," "has," "having," or any other variation thereof are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or more, and the singular also includes the plural unless it is obvious that it is meant otherwise.

Further, use of the term "plurality" is meant to convey "more than one" unless expressly stated to the contrary.

As used herein, qualifiers like "substantially," "about," "approximately," and combinations and variations thereof are intended to include not only the exact amount or value that they qualify but also some slight deviations therefrom, which may be due to manufacturing tolerances, measurement error, wear and tear, stresses exerted on various parts, and combinations thereof, for example.

The use of the term "at least one" or "one or more" will be understood to include one as well as any quantity of more than one. In addition, the use of the phrase "at least one of X, V, and Z" will be understood to include X alone, V alone, and Z alone, as well as any combination of X, V, and Z.

The use of ordinal number terminology (i.e., "first," "second," "third," "fourth," etc.) is solely to differentiate between two or more items, positions, examples, embodiments, or the like, and unless explicitly stated otherwise, is not meant to imply any sequence or order or importance to one item over another or any order of addition.

Finally, as used herein, any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Figure 1:
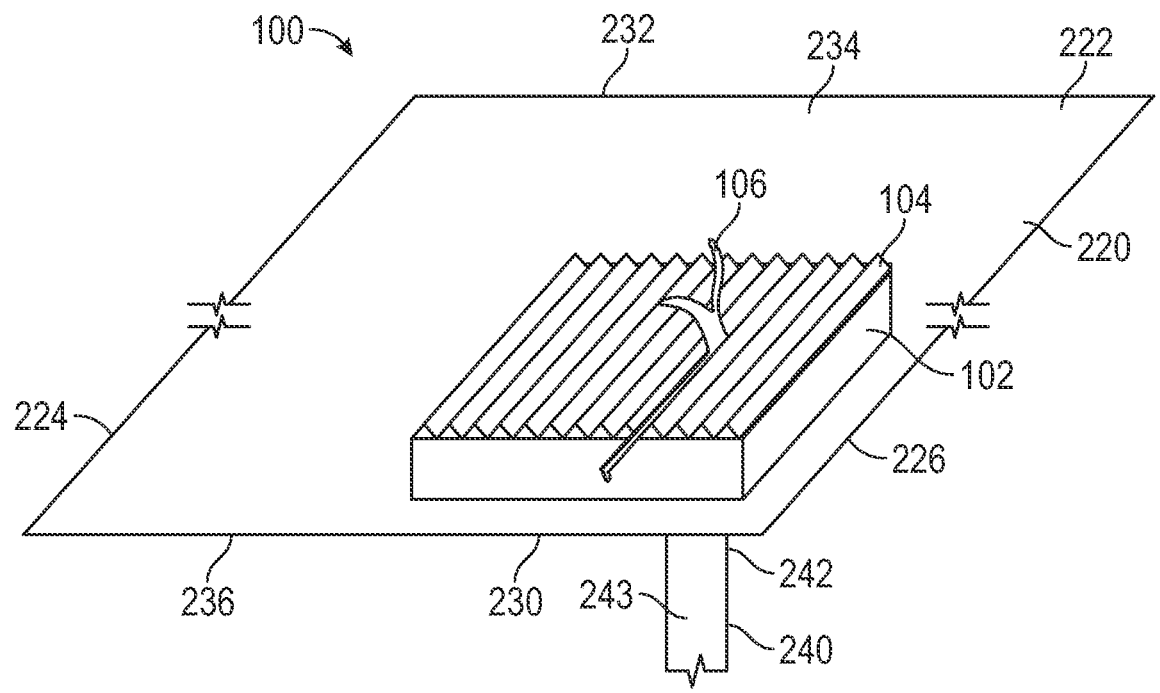
FIG. 1 is a perspective view of an exemplary embodiment of an assembly for supporting at least one surgical instrument used during spinal surgery constructed in accordance with the inventive concepts disclosed herein.
Figure 2:
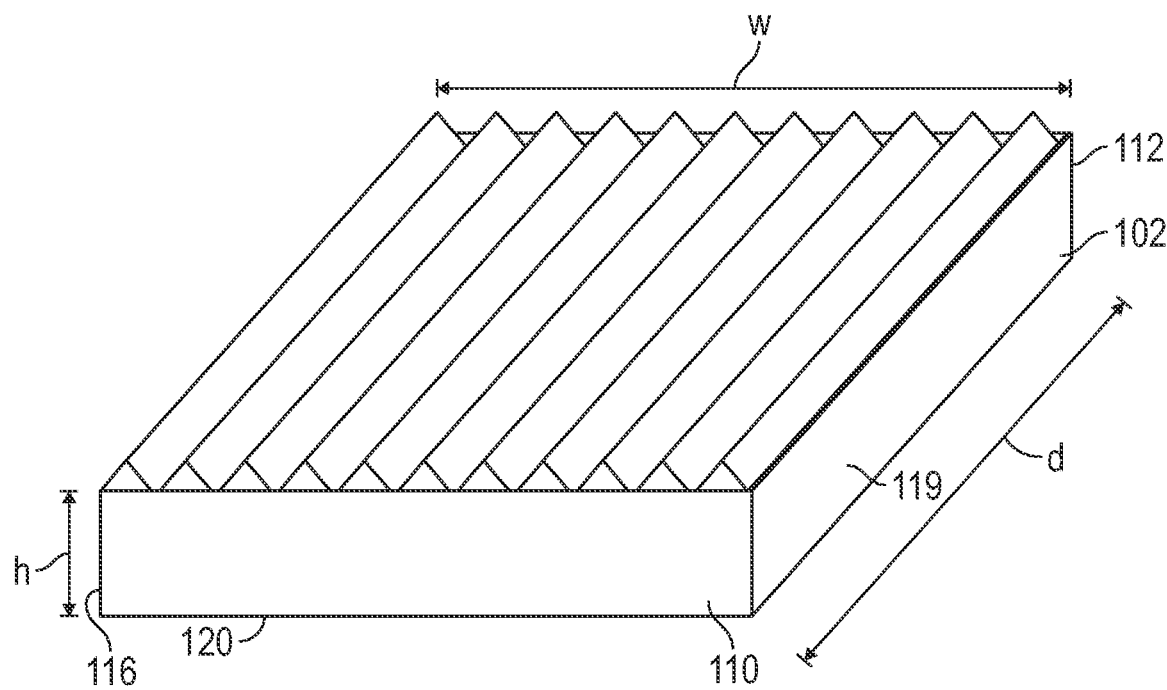
FIG. 2 is a perspective view of the assembly.
Figure 3:
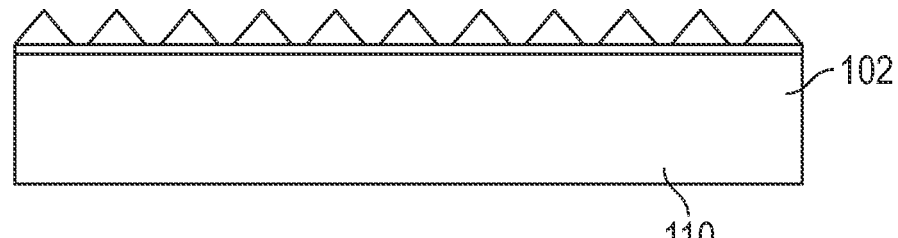
FIG. 3 is a front view of the assembly.
Figure 4:
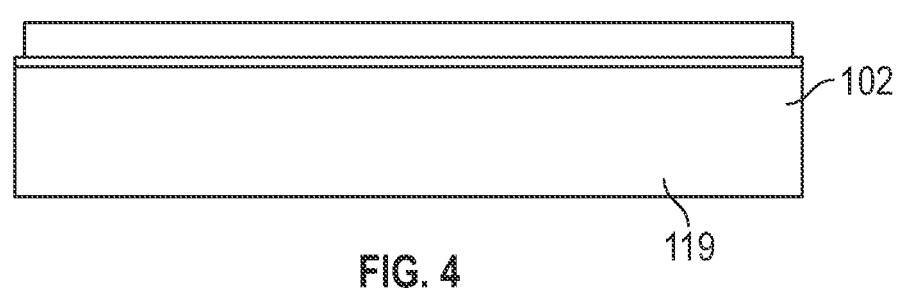
FIG. 4 is a side view of the assembly.

Referring now to the drawings, FIG. 1 illustrates a perspective view of an exemplary embodiment of an assembly 100 for supporting at least one surgical instrument 106 during spinal surgery in accordance with the inventive concepts disclosed herein. Generally, the assembly 100 comprises a receptacle 102 and a support member 104 positioned within the receptacle 102.

Figure 5:
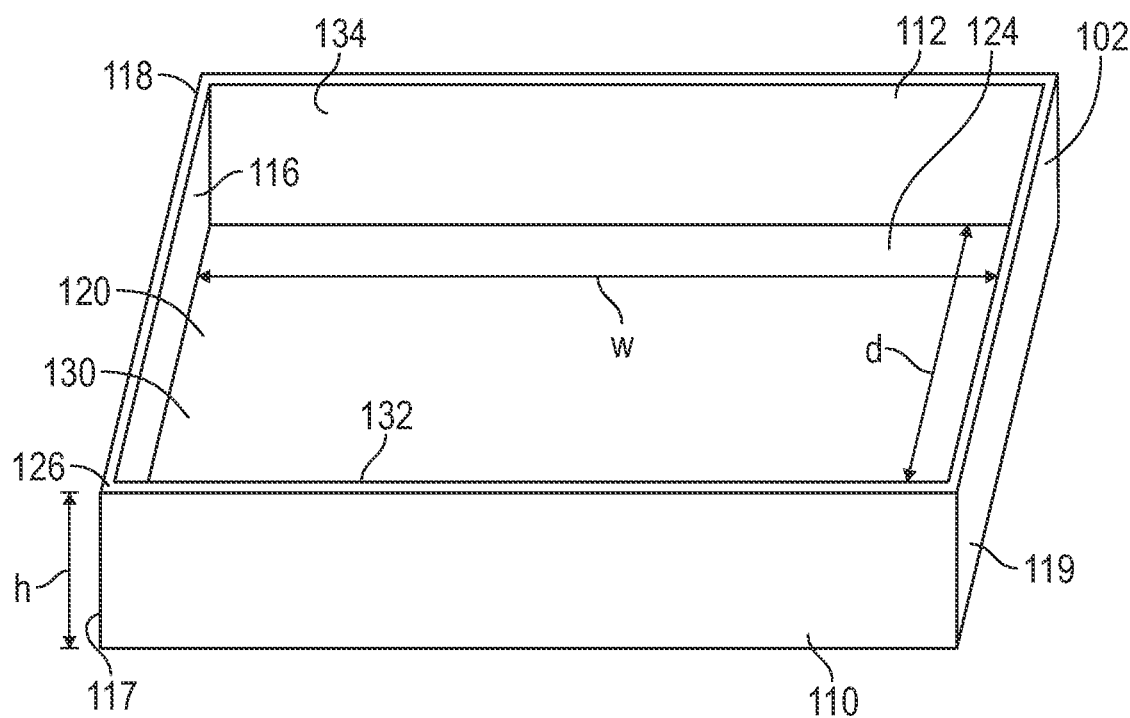
FIG. 5 is a perspective view of an exemplary embodiment of a receptacle of the assembly.

FIG. 5 illustrates a perspective view of an exemplary embodiment of the receptacle 102 of the assembly 100. The receptacle 102 has a front wall 110, a back wall 112 positioned opposite the front wall 110, a first sidewall 116, and a second sidewall 119 opposite the first sidewall 116. The first sidewall 116 and the second sidewall 119 extend between the front wall 110 and back wall 112. A base 120 with a top surface 121 and an opposing bottom surface 122 is positioned perpendicular to and extends between the front wall 110, the back wall 112, the first sidewall 116, and the second sidewall 119, thereby defining a cavity 124. The cavity 124 has a width w extending between the first sidewall 116 and the second sidewall 119, a height h extending between a top end 126 of the front wall 110 and a top surface 121 of the base 120, and a depth d extending from a backside 132 of the front wall 110 to a backside 134 of the back wall 112. In other non-limiting embodiments, the front wall 110 extends between a first end 117 and a second end 118 of the at least one sidewall 116. The base 120 is perpendicular to and extends between the front wall 110 and the at least one sidewall 116, thereby defining the cavity 124. The cavity 124 has the width w extending between the at least one sidewall 116 and the front wall 110, the height h extending between the top end 126 of the front wall 110 and the top surface 121 of the base 120, and a depth d extending from the back side 132 of the front wall 110 to the back side (not shown) of the at least one sidewall 116. The receptacle may be constructed of a metal, plastic, at least one polymer, cellulose, paper, cardboard, or the like.

Figure 6A:
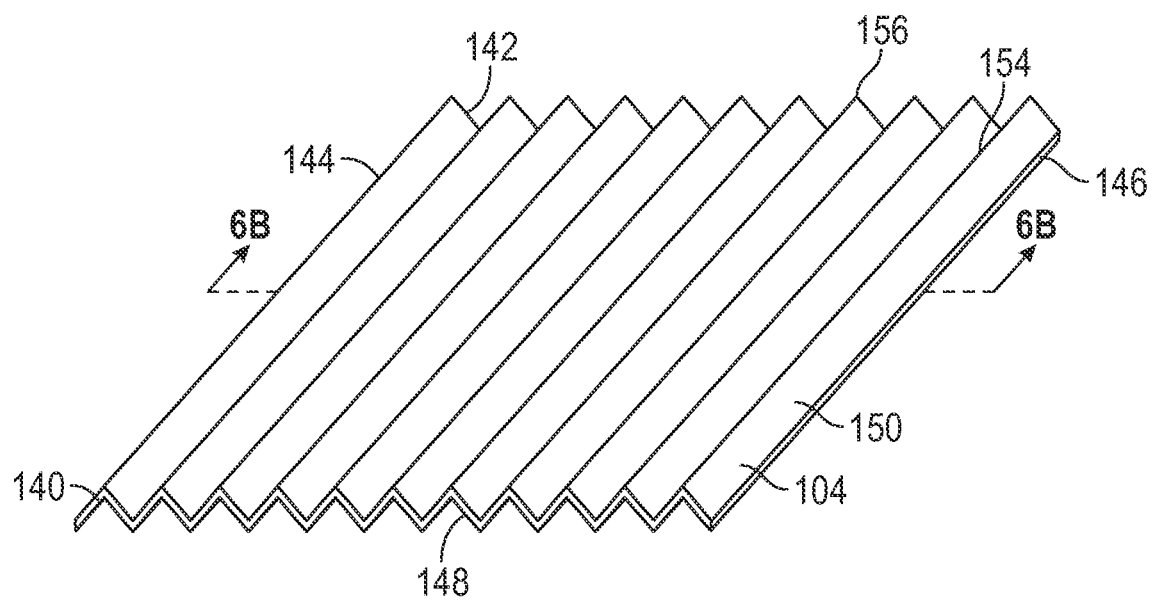
FIG. 6A is a perspective view of an exemplary embodiment of a support member of the assembly.

FIG. 6A illustrates a perspective view of an exemplary embodiment of a support member 104. As seen in FIGS. 1-4, the support member 104 may be positioned within the cavity 124 of the receptacle 102. The exemplary support member 104 has a front end 140, a rear end 142 opposite the front end 140, a first side 144, a second side 146 opposite the first side 144, a bottom side 148, and a top side 150. The top side 150 has a plurality of grooves 154 and ridges 156 extending from the front end 140 to the rear end 142. In one non-limiting embodiment, the grooves 154 and the ridges 156 are in a parallel relationship with one another. The support member is sized so the grooves 154 are positioned below the top end 126 of the front wall 110 of receptacle 102. In some non-limiting embodiments, the support member 104 may be positioned within the cavity 124 of the receptacle 102 such that the bottom side 148 of the support member 104 is positioned on the top surface 130 of the base 120 of the receptacle 102 and the plurality of grooves 154 extend below the top end 126 of the front wall 110 of the receptacle 102. In other non-limiting embodiments, the support member 104 may be positioned within the cavity 124 of the receptacle 102 such that the grooves 154 and ridges 156 of the support member 104 are positioned below the top end 126 of the front wall 110 of the receptacle 102. In other non-limiting embodiments, the support member 104 may be positioned within the cavity 124 of the receptacle 102 such that the ridges 156 of the support member 104 extend above the top end 126 of the front wall 110 of the receptacle 102. In some non-limiting embodiments, the support member 104 may extend the width w of the receptacle 102. In other non-limiting embodiments, the support member 104 may extend a partial width w of the cavity 124 of the receptacle 102. In other non-limiting embodiments, the support member 104 may be packaged in a compressed state in such a way that the plurality of grooves 154 are compressed and thereby positioning a first ridge 156 adjacent a second ridge 156. The support member 104 may be extended into an expanded state upon the application of opposing forces to the first side 144 and the second side 146 of the support member 104 such that the plurality of grooves is no longer in a compressed state.

Figure 6B:
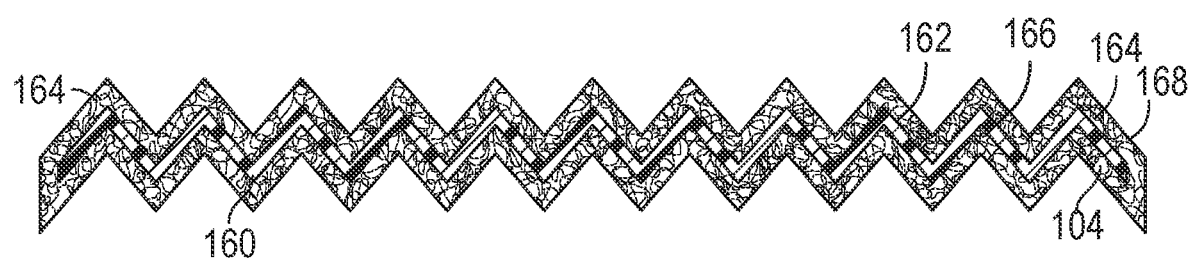
FIG. 6B is a cross-sectional front view of the support member taken along line 6B-6B of FIG. 6A.

FIG. 6B is a cross-sectional front view of the support member taken along line 6B-6B of FIG. 6A. The exemplary support member 104 may have a first layer 160 having an exterior surface 162 and a second layer 164 having an interior surface 166 and an exterior surface 168, wherein the interior surface 166 of the second layer 164 may be positioned on the exterior surface 162 of the first layer 160. In some embodiments, the second layer 164 of the support member 104 may create a frictional relationship between the top side 150 of the support member 104 and the instrument 106 positioned on the top side 150 of the support member 104. In some non-limiting embodiments, the first layer 160 may be a foam, a polymer-based material, plastic, cellulose, cardboard, paper, and the like. In some non-limiting embodiments, the second layer 164 may be a cloth-like material, such as cotton, chiffon, and the like.

Figure 7:
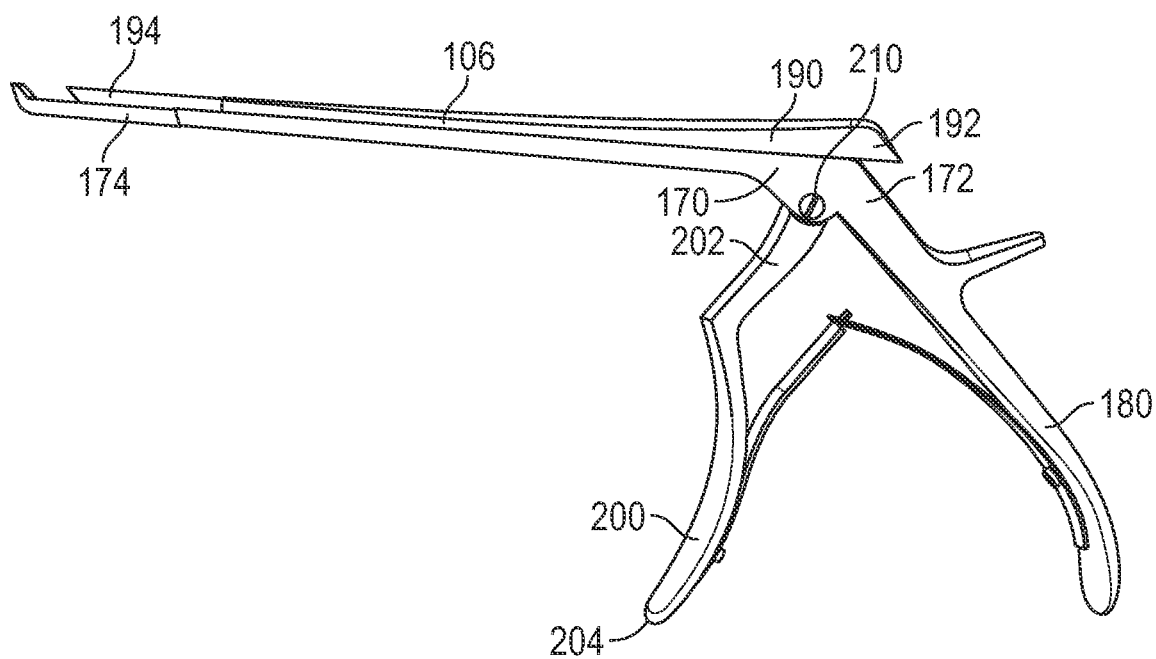
FIG. 7 is a side view of the exemplary embodiment of an instrument used during spinal surgery.

As seen in FIG. 1, generally, the assembly 100 may be in combination with at least one surgical instrument 106, wherein the instrument 106 may be positioned with at least one groove 154 of the support member 104. FIG. 7 illustrates a side view of an exemplary embodiment of the instrument 106 used during spinal surgery. The exemplary surgical instrument 106 has a body 170 having a stationary arm proximal end 172 and an opposing stationary arm distal end 174 and a rear handle member 180 extending at an angle from the stationary arm proximal end 172, and a movable arm 190 slidably coupled to the body 170. The movable arm 190 has a proximal end 192 and an opposing movable arm distal end 194. A forward handle member 200 has a first end 202 and an opposing second end 204. The first end 202 of the forward handle member 200 is connected to the proximal end 192 of the movable arm 190, and the forward handle member 200 is pivotally connected to the rear handle member 180 via a connector 210. In some non-limiting embodiments, the connector 210 may be a pin, a screw, or the like. In some non-limiting embodiments, the at least one surgical instrument 106 may be constructed of metal, polymer, plastic, or the like. In some non-limiting embodiments, the at least one surgical instrument 106 may be a pituitary rongeur, a Kerrison rongeur, or the like.

It will be understood that the assembly 100 may be used to support a plurality of surgical instruments 106. Multiple sizes of surgical instruments 106 may be required during a surgical procedure. The assembly 100 enables a plurality or a set of surgical instruments 106 of various sizes and lengths to be organized so a desired surgical instrument can be swiftly and accurately retrieved from the assembly 100.

In some non-limiting embodiments, as seen in FIG. 1, the assembly 100 may be in combination with a surgical stand 220, such as a mayo stand. The surgical stand 220 has a tray member 222 having a first end 224, a second end 226 opposing the first end 224, a front side 230, a rear side 232 positioned opposing the front side 230, a top surface 234, and a bottom surface 236 positioned opposing the top surface 234. A base member 240 may have a first end 242 connected to the bottom surface 236 of the tray member 222, a second end (not shown) positioned opposing the first end 242, and an intermediate member 243 extending between the first end 242 and the second end. The second end of the base member 240 may be positioned on a surface, thereby positioning the tray member 222 substantially parallel to the surface.

A method for positioning the at least one surgical instrument 106 for use during spinal surgery generally comprises positioning the support member 104 in the receptacle 102 such that the support member 104 may be positioned within the cavity 124 of the receptacle 102 and positioning the at least one surgical instrument 106 in one of the plurality of grooves 154 of the support member 104 in an inverted orientation such that the rear handle member 180 and the forward handle member 200 of the surgical instrument 106 may extend substantially vertically away from the support member 104. In some non-limiting embodiments, the support member 104 may extend the width w of the cavity 124 of the receptacle 102. In other non-limiting embodiments, the support member 104 may extend a partial width w of the cavity 124 of the receptacle 102. In one embodiment, when positioning more than one surgical instrument 106 on the support member 104, the surgical instruments 106 may be arranged from smallest to largest with the distal ends 174, 194 of the surgical instruments 106 in a stair-step fashion.

In some non-limiting embodiments, the method of positioning the at least one surgical instrument 106 for use during spinal surgery may further comprise positioning the bottom surface 122 of the base 120 of the receptacle 102 on the top surface 234 of the surgical stand 220.

In some non-limiting embodiments, the surgical instrument 106 may be positioned adjacent the front end 140 of the support member 104 such that the proximal end 192 of the movable arm 190 of the at least one surgical instrument 106 may be frictionally engaged with the top side 150 of the support member 104 and a portion of the movable arm distal end 194 may be positioned on the top end 126 of the front wall 110 of the receptacle 102 in a way that the rear handle member 180 and the forward handle member 200 may extend substantially vertically away from the support member 104. In some non-limiting embodiments, a first portion of the surgical instrument 106 may be positioned in one of the plurality of grooves 154 in an inverted orientation adjacent the front end 140 of the support member 104, and a second portion of the surgical instrument 106 may be positioned on the top end 126 of the front wall 110 of the receptacle 102 such that the rear handle member 180 and the forward handle member 200 of the surgical instrument 106 extend substantially vertically away from the support member 104. In other non-limiting embodiments, a first portion of the stationary arm proximal end 172 of the surgical instrument 106 may be positioned near the front end 140 of the support member 104 such that a first portion of the stationary arm proximal end 172 of the surgical instrument 106 may be frictionally engaged with at least one of the plurality of grooves 154 of the top side 150 of the support member 104, wherein a second portion of the stationary arm proximal end 172 may be positioned on the top end 126 of the front wall 110 of the receptacle 102 such that the rear handle member 180 and the forward handle member 200 may be positioned substantially vertically away from the support member 104. In another non-limiting embodiment, the first portion of the stationary arm proximal end 172 of the surgical instrument 106 may be positioned near the rear end 142 of the support member 104 such that the stationary arm proximal end 172 of the surgical instrument 106 may be frictionally engaged with at least one of the plurality of grooves 154 of the top side of the support member 104 and wherein a portion of the movable arm distal end 194 may be positioned on the top end 126 of the front wall 110 of the receptacle such that the rear handle member 180 and the forward handle member 200 of the surgical instrument 106 may extend substantially vertically away from the support member 104.

Although the presently disclosed inventive concepts have been described in conjunction with the specific language set forth herein, many alternatives, modifications, and variations will be apparent to those skilled in the art. Accordingly, it is intended to embrace all such alternatives, modifications, and variations that fall within the spirit and broad scope of the presently disclosed inventive concepts. Changes may be made in the construction and the operation of the various components, elements, and assemblies described herein without departing from the spirit and scope of the presently disclosed inventive concepts.

What is claimed is:

1. An assembly in combination with at least one surgical instrument, the surgical instrument, comprising a body having a stationary arm proximal end and an opposing stationary arm distal end and a rear handle member extending at an angle from the stationary arm proximal end, a movable arm slidably coupled to the body, the movable arm having a movable arm proximal end and an opposing movable arm distal end, and a forward handle member having a first end and an opposing second end, the first end of the forward handle member connected to the proximal end of the movable arm, the forward handle member pivotally connected to the rear handle member, the assembly comprising:

a receptacle having a front wall, a back wall positioned opposite the front wall, a first sidewall, a second sidewall opposite the first sidewall, wherein the first sidewall and the second sidewall extend between the front wall and back wall, a base positioned perpendicular to and extending between the front wall, the back wall, the first sidewall and the second sidewall defining a cavity, wherein the cavity has a width extending a length between the first sidewall and the second sidewall, a height extending between a top end of the front wall and a top surface of the base, and a depth extending from a back side of the front wall to a back side of the back wall; and a support member positioned within the cavity of the receptacle having a front end, a rear end opposite the front end, a first side, a second side opposite the first side, a bottom side, and a top side, the top side having a plurality of grooves and ridges extending from the front end to the rear end, wherein the grooves extend below the top end of the front wall of the receptacle;

wherein the surgical instrument is positioned in at least one of the plurality of grooves of the support member in an inverted orientation such that the proximal end of the movable arm is positioned in the groove adjacent the front end of the support member and a portion of the distal end of the movable arm positioned on the top end of the front wall of the receptacle in a way that the rear handle member and the forward handle member extend substantially vertically away from the support member.

2. The assembly of claim 1, further comprising:

a surgical stand for holding the receptacle, the surgical stand having a tray member having a first end, a second end positioned opposing the first end, a front side, a rear side positioned opposing the front side, a top surface, and a bottom surface positioned opposing the top surface, and a base member having a first end connected to the bottom surface of the tray member, a second end positioned opposing the first end, an intermediate member extending between the first end and the second end, wherein the second end of the base member is positioned on a surface such that the tray member is positioned substantially parallel to the surface.

3. The assembly of claim 1, wherein the surgical instrument is frictionally engaged with the at least one of the plurality of grooves of the top side of the support member and is positioned near the front end of the support member, wherein a first portion of the stationary arm proximal end of the instrument is frictionally engaged with the at least one of the plurality of grooves of the top side of the support member and a second portion of the stationary arm proximal end is positioned on the top end of the front wall of the receptacle such that the rear handle member and the forward handle member are positioned substantially vertically away from the support member.

4. The assembly of claim 1, wherein the support member extends the width of the cavity of the receptacle.

5. The assembly of claim 1, wherein the support member has a first layer comprising a foam.

6. The assembly of claim 5, wherein the first layer of the support member has an exterior surface and wherein the support member further comprises a second layer positioned on the exterior surface of the first layer.

7. The assembly of claim 6, wherein the second layer of the support member is a cloth material.

8. The assembly of claim 1, wherein the at least one instrument used during spinal surgery is a pituitary rongeur usable during spinal surgery.

9. The assembly of claim 1, wherein the at least one instrument used during spinal surgery is a Kerrison rongeur usable during spinal surgery.

10. A method for positioning at least one instrument for use during spinal surgery, comprising:

positioning a support member in a receptacle, wherein the receptacle has a front wall, a back wall positioned opposite the front wall, a first sidewall, a second sidewall opposite the first sidewall, wherein the first sidewall and the second sidewall extend between the front wall and back wall, a base having a top surface and a bottom surface positioned substantially perpendicular to and between the front wall, the back wall, the first sidewall and the second sidewall thereby defining a cavity, wherein the cavity has a width extending a length between the first sidewall and the second sidewall, a height extending between a top end of the front wall and a top surface of the base, and a depth extending from a back side of the front wall to a back side of the back wall and wherein the support member has a front end, a rear end opposite the front end, a first side, a second side opposite the first side, a bottom side, and a top side, wherein the top side has a plurality of grooves and ridges extending from the front end to the rear end and wherein the grooves extend below the top end of the front wall of receptacle; and positioning the instrument in at least one of the plurality of grooves of the support member in an inverted orientation such that a rear handle member and a forward handle member of the surgical instrument extend substantially vertically away from the support member.

11. The method of claim 10, further comprising:
positioning the bottom surface of the base of the receptacle on a top surface of a surgical stand.

12. The method of claim 10, wherein the support member extends the width of the cavity of the receptacle.

13. The method of claim 10, wherein the support member has a first layer comprising a foam.

14. The method of claim 13, wherein the first layer of the support member has an exterior surface and wherein the support member further comprises a second layer positioned on the exterior surface of the first layer.

15. The method of claim 14, wherein the second layer of the support member is a cloth material.

16. The method of claim 10, wherein the at least one instrument is a pituitary rongeur.

17. The method of claim 10, wherein the at least one instrument is a Kerrison rongeur.

* * * * *